US012678109B2

(12) United States Patent
Liu

(10) Patent No.: US 12,678,109 B2
(45) Date of Patent: Jul. 14, 2026

(54) CONTROL METHOD AND CONTROL SYSTEM FOR IMAGE SCANNING, ELECTRONIC APPARATUS, AND STORAGE MEDIUM

(71) Applicant: SHANGHAI UNITED IMAGING HEALTHCARE CO., LTD., Shanghai (CN)

(72) Inventor: Kuo-Yue Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 296 days.

(21) Appl. No.: 18/387,485

(22) Filed: Nov. 7, 2023

(65) Prior Publication Data

US 2024/0148343 A1 May 9, 2024

(30) Foreign Application Priority Data

Nov. 9, 2022 (CN) .......................... 202211400001.6

(51) Int. Cl.
*A61B 6/03* (2006.01)
*G06T 7/00* (2017.01)
(Continued)

(52) U.S. Cl.
CPC ............ *A61B 6/032* (2013.01); *G06T 7/0012* (2013.01); *G06T 7/13* (2017.01); *G06V 10/25* (2022.01); *G06T 2207/10081* (2013.01)

(58) Field of Classification Search
CPC ......... A61B 6/481; A61B 6/482; A61B 6/488; A61B 6/032; A61B 6/00; A61B 6/03;
(Continued)

(56) References Cited

U.S. PATENT DOCUMENTS 9,414,798 B2 * 8/2016 Feuerlein ............... A61B 6/481
2020/0163639 A1 * 5/2020 De Man ................. G06N 3/084
(Continued)

FOREIGN PATENT DOCUMENTS

CN 104138268 A 11/2014
CN 102361592 B 6/2015
(Continued)

OTHER PUBLICATIONS

CN-104138268-A—machine English translation (Year: 2014), Nov. 2014.*
(Continued)

*Primary Examiner* — Vu Le
*Assistant Examiner* — Jessica Yifang Lin

(57) ABSTRACT

A control method and a control system for image scanning, an electronic apparatus, and a storage medium. The control method for image scanning comprises of: configuring a monitoring-layer scanning, and obtaining monitoring-layer images; determining an initial target region in each of the monitoring-layer images, and a target part being located in the initial target region;

identifying the target part in the initial target region, and determining a region corresponding to the identified target part to be a region of interest (ROI); and generating a computed tomography (CT) control parameter based on a CT number of the ROI, and adjusting a trigger time of image scanning according to the CT control parameter.

19 Claims, 9 Drawing Sheets

(51) Int. Cl.
    *G06T 7/13*            (2017.01)
    *G06V 10/25*         (2022.01)

(58) Field of Classification Search
    CPC ..................... G06T 7/13; G06T 7/0012; G06T
                 2207/10081; G06T 7/215; G06V 10/25
    See application file for complete search history.

(56) References Cited

U.S. PATENT DOCUMENTS

| | | | |
|---|---|---|---|
| 2020/0337663 A1* | 10/2020 | Zhang .................. | A61B 6/5211 |
| 2022/0148237 A1* | 5/2022 | Wang ..................... | G06V 10/50 |
| 2022/0381862 A1* | 12/2022 | Yang ...................... | A61B 6/545 |

FOREIGN PATENT DOCUMENTS

| | | | |
|---|---|---|---|
| CN | 111789625 A | | 10/2020 |
| CN | 112365492 A | * | 2/2021 |
| CN | 114098780 A | | 3/2022 |
| WO | 9638815 A1 | | 12/1996 |

OTHER PUBLICATIONS

CN-108514425-B—machine English translation (Year: 2021), Jul. 2021.*
CN-114098780-A—machine English translation (Year: 2022), Mar. 2022.*

* cited by examiner

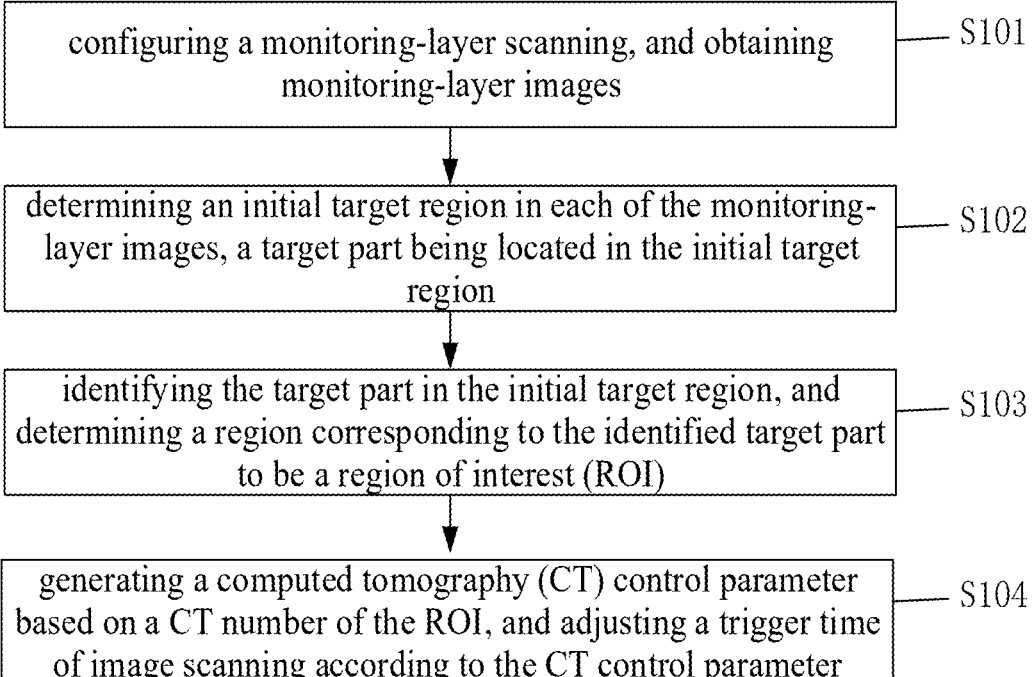

configuring a monitoring-layer scanning, and obtaining monitoring-layer images —— S101 determining an initial target region in each of the monitoring-layer images, a target part being located in the initial target region —— S102 identifying the target part in the initial target region, and determining a region corresponding to the identified target part to be a region of interest (ROI) —— S103 generating a computed tomography (CT) control parameter based on a CT number of the ROI, and adjusting a trigger time of image scanning according to the CT control parameter —— S104

FIG. 1 identifying the second target part in the second initial
target region in each of the monitoring-layer images
based on the first target part       S105a determining the second ROI corresponding to the
second target part       S105b

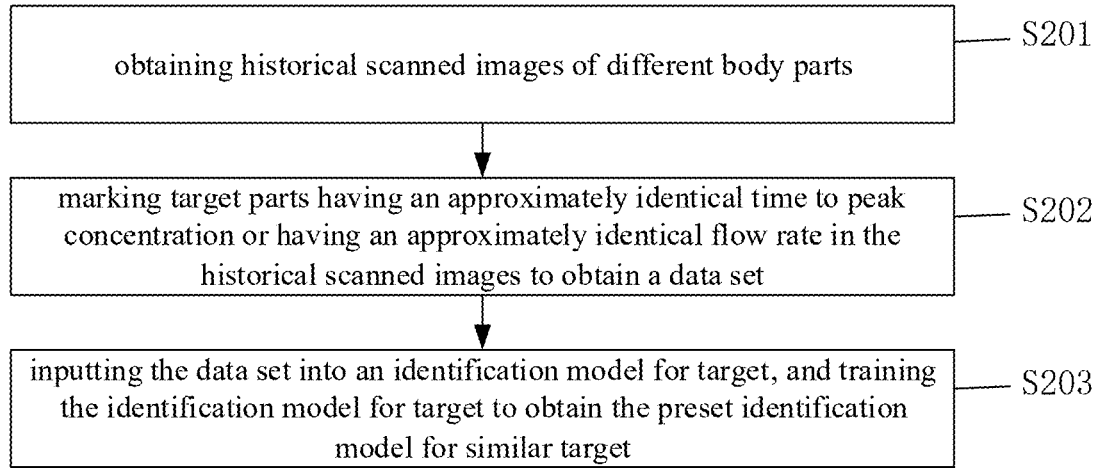

obtaining historical scanned images of different body parts — S201 marking target parts having an approximately identical time to peak concentration or having an approximately identical flow rate in the historical scanned images to obtain a data set — S202 inputting the data set into an identification model for target, and training the identification model for target to obtain the preset identification model for similar target — S203

FIG. 5

CONTROL METHOD AND CONTROL SYSTEM FOR IMAGE SCANNING, ELECTRONIC APPARATUS, AND STORAGE MEDIUM

CROSS-REFERENCE TO RELATED APPLICATION

The present application claims the priority of Chinese patent application No. 202211400001.6, filed on Nov. 9, 2022, and entitled "Triggering Method and Triggering System for Image Scanning, Electronic Apparatus, and Medium", which is incorporated herein by reference in its entirety.

TECHNICAL FIELD

The present disclosure relates to the technical field of computed tomography, specifically to a control method and a control system for image scanning, an electronic apparatus, and a storage medium.

BACKGROUND

Computed Tomography (CT) is a technology of reconstructing images for X-ray tomography data of detected objects by means of computer technology. The CT has the advantages of fast imaging, high density and resolution of reconstructed images, and being convenient to reconstruct three-dimensional images of various sections, etc., and is widely used in medical imaging and other fields currently. One of the technical modes is CT Angiography (CTA) imaging.

During a scan of the CTA, contrast medium will be injected into patient's veins rapidly. According to the blood circulation status of each patient, the CT scanning for the target vessel will be performed at a moment when the contrast medium concentration in the target vessel is optimal, and during the three-dimensional reconstruction, the structures, such as skin, muscles, bones and so on, which need not to be displayed, are moved, and merely the three-dimensional vascular structure and the internal organ structure are displayed. At present, there are four commonly used CTA trigger modes: (1) manual trigger, (2) timing trigger, (3) bolus tracking or monitoring-layer monitoring trigger, and (4) small-dose test bolus tracking trigger.

SUMMARY

The present disclosure provides a control method for image scanning, a control system for image scanning, an electronic apparatus, and a media.

The present disclosure solves the above technical problems through following technical solutions.

The present disclosure provides a control method for image scanning. The control method for image scanning includes configuring a monitoring-layer scanning, and obtaining monitoring-layer images, determining an initial target region in each of the monitoring-layer images, a target part being located in the initial target region, identifying the target part in the initial target region, and determining a region corresponding to the identified target part to be a region of interest (ROI), and generating a computed tomography (CT) control parameter based on a CT number of the ROI, and adjusting a trigger time of image scanning according to the CT control parameter.

In an embodiment of the present application, before the generating the CT control parameter based on the CT number of the ROI and adjusting the trigger time of image scanning according to the CT control parameter, the control method for image scanning further comprises: setting a preset threshold value of the CT number of the ROI.

In an embodiment of the present application, the generating the CT control parameter based on the CT number of the ROI and adjusting the trigger time of image scanning according to the CT control parameter comprises generating the CT control parameter when the CT number of the ROI is within a range related to the preset threshold value, and adjusting the trigger time of image scanning according to the CT control parameter.

In an embodiment of the present application, the range related to the preset threshold value is a range, in which CT numbers are greater than or equal to a difference between the preset threshold value and an adjustment value of the preset threshold value, and are less than or equal to a sum of the preset threshold value and the adjustment value of the preset threshold value.

In an embodiment of the present application, the adjustment value of the preset threshold value is 5%, 10%, 15%, 20%, or 25% of the preset threshold value.

In an embodiment of the present application, the initial target region comprises a first initial target region, the target part comprises a first target part, the ROI comprises a first ROI, the preset threshold value comprises a first preset threshold value, and the range related to the preset threshold value comprises a range related to the first preset threshold value.

The identifying the target part in the initial target region and determining the region corresponding to the identified target part to be the ROI, comprises determining a center point of the first initial target region, extracting similar pixels centered around the center point to identify an edge of the first target part, and determining a region within the edge of the first target part to be the first ROI.

In an embodiment of the present application, the generating the computed tomography control parameter based on the CT number of the ROI and adjusting the trigger time of image scanning according to the CT control parameter, comprises generating the CT control parameter if a CT number of the first ROI is within the range related to the first preset threshold value, and adjusting the trigger time of image scanning according to the CT control parameter.

In an embodiment of the present application, the initial target region further comprises a second initial target region, the target part further comprises a second target part, the ROI further comprises a second ROI, the preset threshold value further comprises a second preset threshold value, and the range related to the preset threshold value further comprises a range related to the second preset threshold value.

After the determining the region within the edge of the first target part to be the first ROI, the control method for image scanning further comprises identifying the second target part in the second initial target region in each of the monitoring-layer images based on the first target part, and determining the second ROI corresponding to the second target part.

In an embodiment of the present application, the first preset threshold value is the same as the second preset threshold value.

In an embodiment of the present application, the range related to the first preset threshold value is the same as the range related to the second preset threshold value, and a time to peak concentration of contrast medium of the second target part is substantially identical to a time to peak concentration of contrast medium of the first target part.

In an embodiment of the present application, the generating the CT control parameter based on the CT number of the ROI and adjusting the trigger time of image scanning according to the CT control parameter, comprises: generating the CT control parameter if a CT number of the second ROI is within the range related to the second preset threshold value, and adjusting the trigger time of image scanning according to the CT control parameter.

In an embodiment of the present application, the identifying the second target part in the second initial target region in each of the monitoring-layer images based on the first target part and determining the second ROI corresponding to the second target part, comprises identifying the second target part in the second initial target region in each of the monitoring-layer images based on the first target part and a preset similar-target identification model, and determining a region within an edge of the second target part to be the second ROI.

In an embodiment of the present application, before the identifying the second target part in the second initial target region in each of the monitoring-layer images based on the first target part and the preset similar-target identification model, the control method for image scanning further comprises obtaining the preset similar-target identification model through training. The obtaining the preset similar-target identification model through training comprises: obtaining historical scanned images of different body parts, marking target parts having an substantially identical time to peak concentration or having an substantially identical flow rate in the historical scanned images to obtain a data set, and inputting the data set into an identification model for target, and training the identification model for target to obtain the preset similar-target identification model.

In an embodiment of the present application, the setting the preset threshold value of the CT number of the ROI comprises: determining the preset threshold value of the CT number of the ROI based on a proposed model for preset threshold value, or obtaining the preset threshold value of the CT number of the ROI based on medical experience.

In an embodiment of the present application, the range related to the first preset threshold value is a range, in which CT numbers are greater than or equal to a difference between the first preset threshold value and an adjustment value of the first preset threshold value, and are less than or equal to a sum of the first preset threshold value and the adjustment value of the first preset threshold value. The adjustment value of the first preset threshold value is 20% of the first preset threshold value.

In an embodiment of the present application, the range related to the second preset threshold value is a range, in which CT numbers are greater than or equal to a difference between the second preset threshold value and an adjustment value of the second preset threshold value, and are less than or equal to a sum of the second preset threshold value and the adjustment value of the second preset threshold value. The adjustment value of the second preset threshold value is 20% of the second preset threshold value.

In an embodiment of the present application, the initial target region comprises a plurality of second initial target regions, the target part comprises a plurality of second target parts, the ROI comprises a plurality of second ROIs, the preset threshold value comprises a plurality of second preset threshold values, and the range related to the preset threshold value comprises a plurality of ranges related to the plurality of second preset threshold values, respectively.

After the determining the region within the edge of the first target part to be the first ROI, the control method for image scanning further comprises: identifying the plurality of second target parts in the plurality of second initial target regions in each of the monitoring-layer images based on the first target part, and determining the plurality of second ROIs corresponding to the plurality of second target parts, respectively.

In an embodiment of the present application, the generating the CT control parameter based on the CT number of the ROI and adjusting the trigger time of image scanning according to the CT control parameter, comprises: obtaining the CT number of the first ROI or the CT number of the second ROI, and increasing a sampling frequency of image when the CT number of the first ROI is within the range related to the first preset threshold value, or when the CT number of the second ROI is within the range related to the second preset threshold value.

The present disclosure further provides a control system for image scanning including an image obtaining module, an initial-target-region determining module, an ROI determining module, and an image scanning control module.

The image obtaining module is configured to configure a monitoring-layer scanning, and obtain monitoring-layer images.

The initial-target-region determining module is configured to determine an initial target region in each of the monitoring-layer images. A target part is located in the initial target region.

The ROI determining module is configured to identify the target part in the initial target region, and determine a region corresponding to the identified target part to be the ROI.

The image scanning control module is configured to generate a CT control parameter based on the CT number of the ROI, and adjust a trigger time of image scanning according to the CT control parameter.

In an embodiment of the present disclosure, the ROI includes a first ROI, and the target part includes a first target part, the determined ROI includes the first ROI, the preset threshold value includes the first preset threshold value, and the range related to the preset threshold value includes the range related to the first preset threshold value.

The ROI determining module is further configured to determine a center point of the first initial target region, extract similar pixels centered around the center point to identify an edge of the first target part, and determine a region within the edge of the first target part to be the first ROI.

The image scanning control module is further configured to generate a CT control parameter if the CT number of the first ROI is within the range related to the first preset threshold value, and adjust the trigger time of image scanning according to the CT control parameter.

In an embodiment of the present disclosure, the initial target region further includes a second initial target region, and correspondingly, the target part further includes a second target part, the determined ROI further includes a second ROI, the preset threshold value further includes a second preset threshold value, and the range related to the preset threshold value further includes the range related to the second preset threshold value. A time to peak concentration of the contrast medium of the second target part is substantially identical to the time to peak concentration of the contrast medium of the first target part.

The ROI determining module is further configured to identify the second target part in the second initial target region in the monitoring-layer image based on the first target part, and determine the second ROI corresponding to the second target part.

The image scanning control module 4 is further configured to generate the CT control parameter if the CT number of the second ROI is within the range related to the second preset threshold value, and adjust the trigger time of image scanning according to the CT control parameter.

In an embodiment of the present disclosure, the ROI determining module is further configured to identify the second target part in the second initial target region in the monitoring-layer image based on the first target part and a preset similar-target identification model, and determine a region within the edge of the second target part to be the second ROI.

In an embodiment of the present disclosure, the control system for image scanning further includes a model training module.

The model training module is configured to obtain historical scanned images of different body parts, mark target parts having a substantially identical time to peak concentration or a substantially identical flow rate in the historical scanned images to obtain a data set, and input the data set into an identification model for target, and train the identification model for target to obtain the preset similar-target identification model.

In an embodiment of the present disclosure, the control system for image scanning further includes a threshold value setting module.

The threshold value setting module is configured to determine the preset threshold value corresponding to the target part based on a proposed model for preset threshold value, or obtain the preset threshold value of the CT number of the ROI based on medical experience.

In an embodiment of the present disclosure, the control system further includes a trigger-time adjusting module. The trigger-time adjusting module 7 is configured to obtain the CT number of the first ROI or second ROI, and adjust the trigger time of image scanning for the monitoring layer according to the CT number.

The present disclosure further provides an electronic apparatus, comprising a memory, a processor, and a computer program stored in the memory and executable by the processor. The processor, when executing the computer program, executes steps of any one of the control methods for image scanning above.

The present disclosure further provides a non-transitory computer-readable storage medium, having a computer program stored thereon. The computer program, when executed by a processor, causes the processor to execute steps of any one of the control methods for image scanning above.

The positive progressive effect of the present disclosure is: by setting monitoring-layer scanning, the monitoring-layer image is obtained; Determine an initial target region in the monitoring-layer image, and the initial target region includes a target part; identify the target part in the initial target region, and determine the region corresponding to the identified target part as the region of interest; generate CT control parameter according to the CT number of the ROI, and control the trigger time of image scanning according to the CT control parameter. It can accurately determine the region of interest corresponding to the target part, and then determine the best scanning time point, achieving the accurate determination of the trigger time point of image scanning with the best region of interest scanning effect.

BRIEF DESCRIPTION OF THE DRAWINGS

FIG. 1 is a schematic first flow chart of a control method for image scanning according to an embodiment of the present disclosure.

FIG. 5 is a schematic fourth flow chart of the control method for image scanning according to an embodiment of the present disclosure.

DETAILED DESCRIPTION OF THE EMBODIMENTS

Figure 2:
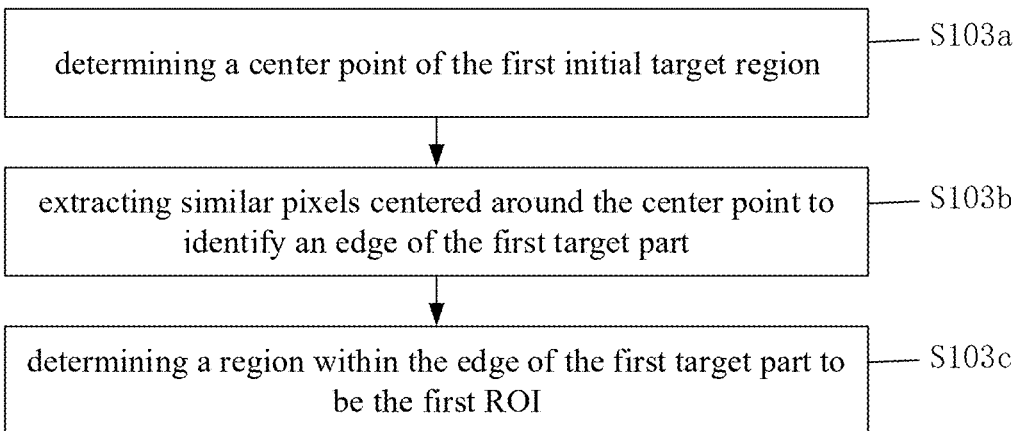
FIG. 2 is a schematic second flow chart of the control method for image scanning according to an embodiment of the present disclosure.

The present disclosure is further described hereinafter through embodiments, but is not limited within the scope of the embodiments.

"An embodiment" mentioned in the present disclosure means that a particular feature, a structure or a characteristic described combining with the embodiment may be included in at least one of the embodiments of the application. This phrase described in various places of the specification is not necessarily referring to the same embodiment, an embodiment mutually exclusive with or separate from other embodiments, or an alternative embodiment. It should be explicitly and implicitly understood by those skilled in the art that the embodiments described herein may be combined with other embodiments.

According to CTA protocols, it is generally required that scanning should be performed when the contrast medium concentration in the target vessel reaches a peak value to obtain the optimal image result. However, the time points, when concentrations of the contrast mediums in different patients or in different vessels of different parts reach peak values, are not completely consistent. Therefore, before the CTA scanning is performed, the contrast medium concentrations in the vessels will be tracked to determine when the CTA scanning starts. The tracking process takes a time period. In the tracking process, if the patient makes actions like swallowing, breathing, etc., or the patient moves slightly without being noticed by the operator, the position where the contrast medium concentration is planned to be observed will change, thus bringing a result that changes in the contrast medium concentration may not be accurately observed.

In the related art, a timed trigger refers to setting an empirical time value based on experience, which requires a technician to have rich experience to set the empirical time value. For a body part where a blood flow rate is very fast, it is very difficult to capture the time to peak concentration.

The bolus tracking mode detects the time to peak concentration of the contrast medium by detecting a CT number of an upstream vessel. However, when the vessels in the monitoring layer are very small, it is very difficult to accurately determine the position where the contrast medium concentration is to be detected. In addition, due to the slight movement of the patient, it may be impossible to accurately detect the changes in the contrast medium concentration, thus resulting in a capture of an inaccurate time to peak concentration. In the mode of the small-dose bolus tracing, a small dose of contrast medium needs to be injected first, and the whole flow of the contrast medium should be detected, and then the time is set. It is often necessary to inject the contrast medium twice, and the monitoring layer should be scanned for several times, thus causing a relatively high radiation dose. In addition, there should be a time period between two scans, thus causing a long overall examination time and a cumbersome operation, which is not applicable to application scenarios of an emergency. Therefore, the CTA trigger modes in the prior art all have the problem of being unable to accurately determine the time to peak concentration, which in turn leads to the problems that the optimal scanning time point cannot be determined, and that a clearly developed scanned image cannot be obtained.

Based on this, an embodiment provides a control method for image scanning. It should be noted that steps shown in the flow charts in the attached drawings may be executed in a computer system such as a set of computer-executable instructions. In addition, although logical orders are shown in the flow chart, in some cases, these steps shown or described may be performed in a different order from the orders therein.

The control method for image scanning provided by this embodiment may be executed in an image scanning device, a computer terminal, a network device, a chip, a chip module, or a similar computing device. A control device for image scanning may be implemented by software and/or hardware.

As shown in FIG. 1, the control method for image scanning according to an embodiment of the present disclosure includes the following steps S101 to S104.

In step S101, a monitoring-layer scanning is configured, and monitoring-layer images are obtained.

It should be noted that the monitoring-layer scanning is used for monitoring changes in CT numbers of a target part, that is, the changes in concentrations of the contrast medium in the target part. An image of a layer-plane, which may be, but not limited to, an axial image, or a sagittal image, may be obtained first through an axial scan. Specifically, the monitoring-layer scanning is to make continuous exposures for the same region/part to obtain monitoring-layer images at different time points, so as to determine a region of interest (ROI) based on the monitoring-layer images at different time points. The same part is scanned several times to obtain two-dimension images, and an exposure interval is 2 s. The exposure interval for the monitoring layer will be shortened to 0.5 s, when it is detected that the CT number of the ROI falls within a range related to the preset threshold value. In an embodiment, the range is defined as CT numbers that are within $\pm 20\%$ of the preset threshold value. For example, the CT numbers are greater than or equal to a difference between the preset threshold value and 20% of the preset threshold value, and less than or equal to a sum of the preset threshold value and 20% of the preset threshold value. In an embodiment, the preset threshold value is 100, then the range related to the preset threshold value is from 80 to 120.

For example, the patient's target part may be first scanned to obtain a positioning image, for example, in the head and neck CTA scanning, the neck needs to be positioned. A position of the positioning image is selected based on the scanned positioning image, and the position of the monitoring layer is determined based on the position of the positioning image by, for example, dragging a scanning frame to change a position of the scanning frame. Then the contrast medium is injected, and continuous exposures are made to monitor and obtain the monitoring-layer image of the neck.

It should also be noted that the contrast medium is a chemical product injected into human tissues or organs to enhance the visibility of images, or the contrast medium is taken orally by the patient and enters the patient's body. Because a density of the contrast medium is higher or lower than those of the surrounding tissues, the monitoring-layer images may be obtained by means of some medical apparatus. These medical apparatuses mainly refer to medical image scanning devices, such as devices using computed tomography, any other scanning mode, or a combination thereof.

In step S102, an initial target region is determined in the monitoring-layer image, and a target part is located in the initial target region.

The initial target region, namely an initial region in which the target part is located, is determined in the monitoring-layer image. The initial region may be a region selected by the user roughly, and the roughly selected region is a closed region. For example, the user may draw or circle the target part in the monitoring-layer image through an input device, or a rough region may be automatically pre-selected based on the scanned project combining with historical data and human body data. For example, in the head and neck CTA scanning, a region of the carotid artery or a region of the vertebral artery in the neck may be pre-selected, which is also applicable to a coronary artery CTA, a cerebrovascular CTA, and a pulmonary artery CTA, which is not limited by the embodiments of the present disclosure. The determining the initial target region automatically or manually is provided by the embodiments of the present disclosure, so that even an inexperienced user may perform the operation, thereby improving user experience.

In step S103, the target part in the initial target region is identified, and a region corresponding to the identified target part is determined to be the region of interest (ROI).

The target part is identified based on the initial target region determined by the user. Different tissue structures have different densities, shapes, and sizes, therefore pixels with similar CT numbers may be extracted based on the above characteristics, so that the edge of the target part may be identified, thereby obtaining an accurate region corresponding to the target part, and determining the region corresponding to the target part to be the ROI. In this way, even if the patient makes actions or slightly moves in the CTA scanning process without being noticed by the operator, real-time calculations may be performed to dynamically determine the ROI every time the monitoring layer is scanned, thereby ensuring the ROI is accurately monitored, and establishing a basis for accurately determining the time to peak concentration of the target part.

In step S104, a CT control parameter is generated based on the CT number of the ROI, and a trigger time of image scanning is adjusted according to the CT control parameter.

The trigger time of image scanning is the CT sampling and exposure time point. The CT sampling and exposure time point is adjusted according to the CT control parameter, so as to trigger the CT scanning according to the trigger time of image scanning.

In some embodiments, the CT control parameter may be generated when the CT number of the ROI is within a range related to the preset threshold value. In some embodiments, the range related to the preset threshold value is a range in which the CT numbers are greater than or equal to a difference between the preset threshold value and an adjustment value of the preset threshold value, and are less than or equal to a sum of the preset threshold value and the adjustment value of the preset threshold value. In some embodiments, the adjustment value of the preset threshold value is 20% of the preset threshold value. For example, if the preset threshold value is 100, then the adjustment value of the preset threshold value is 20, and the range related to the preset threshold value is from 80 to 120. In some embodiments, the adjustment value of the preset threshold value may be 5%, 10%, or 15%, or 25% of the preset threshold value. In some embodiments, the CT control parameter is a switching signal. For example, when the switching signal is 1, the CT scanning is triggered.

It should be noted that the CT number is represented by a specific unit, generally a number called Hounsfield unit (HU), and represents the density of a certain local tissue or organ in the human body. The contrast medium may be gas contrast medium or liquid contrast medium. The density of the liquid contrast medium is generally higher than the densities of the surrounding human tissues, and the density of the gas contrast medium is generally lower than the densities of the surrounding human tissues. In order to obtain the images with the optimal effect, the image scanning generally starts when the contrast medium concentration in the vessel in the target region is relatively high, that is, when the CT number of the target region (e.g., a vessel) is at a relatively high level.

The embodiment of the present disclosure may accurately determine the corresponding ROI of the target part, and then determine the optimal scanning time point. That is, when the CT number of the ROI is within the range related to the preset threshold value, the trigger time of image scanning is adjusted, thereby accurately determining the ROI, obtaining the trigger time that enables the scanning effect to be the optimal, and obtaining the optimal image data.

As an optional implementation of the present disclosure, the initial target region includes a first initial target region, and correspondingly, the target part includes a first target part, the determined ROI includes a first ROI, the preset threshold value includes a first preset threshold value, and the range related to the preset threshold value includes a range related to the first preset threshold value. In some embodiments, the first target part may be a vessel or an organ.

As shown in the embodiment of FIG. 2, step S103 of identifying the target part in the initial target region and determining the region corresponding to the identified target part to be the ROI includes steps S103a to step S103c.

In step S103a, a center point of the first initial target region is determined.

A geometric center of the first initial target region determined by the user is extracted and is determined to be the center point of the first initial target region. The initial target region is generally in a shape of an ellipse or a circle, or has an irregular shape. For example, if the first initial target region determined by the user is in the shape of a circle, then the center point of the first initial target region is the center of the circle.

In step S103b, similar pixels centered around the center point are extracted to identify an edge of the first target part.

Figure 4:
FIG. 4 is a schematic diagram showing similar targets according to an embodiment of the present disclosure.

The operation of pixel erosion and expansion is performed by means of spreading from the determined center point of the first initial target region to extract similar pixels nearby, so that a boundary or edge of the first target part is identified. In some embodiments, the first target part is a target vessel. As shown in FIG. 4, the target vessel A is the first target part, and the edge of the first target part is identified.

In step S103c, a region within the edge of the first target part is determined to be the first ROI.

The outcome of processing is updated and displayed as the first ROI, so that the time to peak concentration of the contrast medium of the first target part is accurately monitored.

In an embodiment of the present disclosure, the step S104 includes step S104a.

In step S104a, if the CT number of the first ROI is within the range related to the first preset threshold value, the CT control parameter is generated, and the trigger time of image scanning is adjusted according to the CT control parameter. In an embodiment of the present disclosure, if the CT number of the first ROI within the ROI is within the range related to the first preset threshold value, the CT control parameter is generated to adjust the trigger time of image scanning. In some embodiments, the range related to the first preset threshold value is a range in which CT numbers are greater than or equal to a difference between the first preset threshold value and an adjustment value of the preset threshold value, and are less than or equal to a sum of the first preset threshold value and the adjustment value of the preset threshold value. In some embodiments, the adjustment value of the preset threshold value is 20% of the first preset threshold value.

According to the embodiments of the present disclosure, after the rough region is determined, the region corresponding to the first target part may be accurately identified and is determined to be the first ROI, then it may be determined whether the CT number of the first ROI is within the range related to the first preset threshold value, so as to determine whether the trigger time of image scanning needs to be adjusted or not.

In another optional embodiment of the present disclosure, the initial target region further includes a second initial target region, and correspondingly, the target part further includes a second target part, the determined ROI further includes a second ROI, the preset threshold value further includes a second preset threshold value, and the range related to the preset threshold value further includes the range related to the second preset threshold value. In an embodiment, a time to peak concentration of the contrast medium of the second target part is substantially identical to the time to peak concentration of the contrast medium of the first target part. In an embodiment, the second target part may be a vessel or an organ. In an embodiment, the first preset threshold value is the same as the second preset threshold value. In an embodiment, the first preset threshold value is different from the second preset threshold value. In an embodiment, the range related to the first preset threshold value is the same as the range related to the second preset threshold value, and the time to peak concentration of the contrast medium of the second target part is substantially identical to the time to peak concentration of the contrast medium of the first target part.

It should be noted that the second initial target region is not limited to one part or one region, and may include a plurality of parts or regions, that is, as long as a part or region (e.g., a vessel or an organ) and the first target part have the substantially identical time to peak concentration of the contrast medium, the part or region may be used as the second ROI. Therefore, the number of the second initial target regions is not limited in the embodiments of the present disclosure. As shown in FIG. 4, the target vessels B are the second target parts, namely the parts similar with the first target part. Three second target parts are identified, and correspondingly, three second initial target regions are determined.

After step S103, the control method for image scanning according to an embodiment of the present disclosure further includes step S105.

In step S105, the second target part in the second initial target region in the monitoring-layer image is identified based on the first target part, and the second ROI corresponding to the second target part is determined.

Identify and segment the anatomical locations on the same monitoring layer, and all similar parts, namely the second target parts, like vessels or organs, are extracted. The similar vessels refer to the vessels, through which the blood flows by taking the substantially identical flow time period during a blood circulation, thus the similar vessels may be used to determine the time to peak concentration of the contrast medium.

Figure 3:
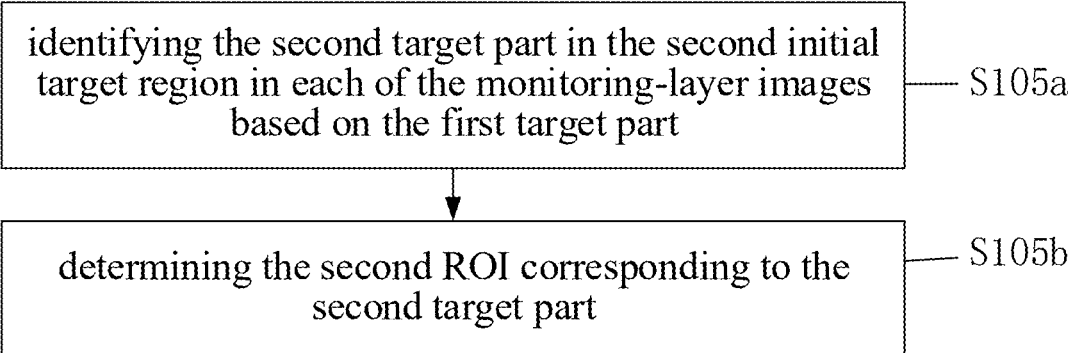
FIG. 3 is a schematic third flow chart of the control method for image scanning according to an embodiment of the present disclosure.

In an optional embodiment, as shown in FIG. 3, the step S105 of this embodiment includes step S105a and step S105b.

In step S105a, the second target part in the second initial target region in the monitoring-layer image is identified based on the first target part and a preset similar-target identification model.

As shown in FIG. 4, the left and right common carotid arteries and the left and right vertebral arteries in the neck have a substantially identical time to peak concentration, so no matter which one of the vessels is used as the first target part (A denotes the target vessel), the other three vessels may be used as the second target parts (B denotes a similar vessel).

In step S105b, a region within the edge of the second target part is determined to be the second ROI.

It should also be noted that the second target part in the second initial target region in the monitoring-layer image is identified based on the first target part and the preset similar-target identification model. After the second target part is determined, the second initial target region is updated in real time to obtain the second ROI. An updating process of the second initial target region is similar to the updating process of the first initial target region in which the similar pixels from the center point to the edge are extracted, and will not be repeated hereinafter.

In some embodiments of the present disclosure, before step S105a of identifying the second target part in the second initial target region in the monitoring-layer image based on the first target part and the preset similar-target identification model, the control method for image scanning further includes a step of obtaining the preset similar-target identification model through training. The preset similar-target identification model is obtained through training. As shown in FIG. 5, the step of obtaining the preset similar-target identification model through training according to an embodiment of the present disclosure includes step S201 to step S203.

In step S201, historical scanned images of different body parts are obtained.

In step S202, target parts having a substantially identical time to peak concentration or a substantially identical flow rate in the historical scanned images are marked to obtain a data set.

In step S203, the data set is inputted into an identification model for target, and the identification model for target is trained to obtain the preset similar-target identification model.

It should be noted that the data set mainly includes enhanced scanned images obtained after the contrast medium is injected. These enhanced scanned images obtained at different time points are analyzed to identify vessels having the substantially identical time to peak concentration in different body parts, and these vessels are marked.

It should be noted that the identification model for target includes, but is not limited to, one or more of a RetinaNet model (a detection model for target), a Region-CNN (R-CNN) model (an algorithm model that applies deep learning to a target detection), a Feature Pyramid Network (FPN) model, and a YOLO V3 model (a detection model for target).

In an embodiment of the present disclosure, step S104 further includes a step S104b.

In step S104b, if the CT number of the second ROI is within the range related to the second preset threshold value, the CT control parameter is generated, and the trigger time of image scanning is adjusted according to the CT control parameter.

In an embodiment of the present disclosure, the CT control parameter may also be generated when the CT number of the second ROI within the ROI is within the range related to the second preset threshold value, so as to adjust the trigger time of image scanning. It should also be noted that, in some embodiments of the present disclosure, the second preset threshold value of the second ROI may be different from the first preset threshold value of the first ROI.

In some embodiments of the present disclosure, the initial target region includes a plurality of second initial target regions, and the target part includes a plurality of second target parts, the ROI includes a plurality of second ROIs, the preset threshold value includes a plurality of second preset threshold values, and the range related to the preset threshold value includes a plurality of ranges related to the plurality of second preset threshold values respectively. After the step S103c of determining the region within the edge of the first target to be the first ROI, the control method further includes: identifying the plurality of second target parts in the plurality of second initial target regions in the monitoring-layer image respectively based on the first target part, and determining the plurality of second ROIs corresponding to the plurality of second target parts respectively. In these embodiments, the similar parts in the same layer-plane, namely the second target parts, may be extracted to identify the plurality of second ROIs and trigger the scanning, thereby solving the problem that the ROIs in small vessels in the body part cannot be precisely positioned because the contrast medium is not full and the CT number is inaccurate, which is caused by pathologic factors such as plaques in target vessels, calcification of the target vessels, etc. Thus the time to peak concentration of the contrast medium is accurately captured by using the similar parts, thereby guaranteeing of obtaining the optimal image data.

In some embodiments of the present disclosure, before the step S104 of generating the CT control parameter based on the CT number of the ROI and adjusting the trigger time of image scanning according to the CT control parameter, the control method for image scanning includes setting the preset threshold value of the CT number of the ROI.

In some embodiments, setting the preset threshold value of the CT number of the ROI includes determining the preset threshold value of the CT number of the ROI based on a proposed model for preset threshold value. In some embodiments of the present disclosure, the setting the preset threshold value of the CT number of the ROI includes: obtaining the preset threshold value of the CT number of the ROI based on medical experience. The preset threshold value may be set based on known medical experience, and a specific value thereof depends on different to-be-scanned target parts of different patients and is not specifically limited in the embodiments of the present disclosure.

It should be noted that the threshold value setting modes of the embodiments of the present disclosure include a manual mode and an auto mode. The range related to the preset threshold value is a range in which the CT numbers are greater than or equal to the difference between the preset threshold value and the adjustment value of the preset threshold value, and are less than or equal to the sum of the preset threshold value and the adjustment value of the preset threshold value. The manual mode means that the user needs to set the preset threshold value manually. When the CT number of the target part is within the range related to the first preset threshold value, the trigger time of image scanning may be adjusted. When the CT number of the similar target is within the range related to the second preset threshold value, namely the range in which the CT numbers are greater than or equal to the difference between the second preset threshold value and the adjustment value of second preset threshold value, and are less than or equal to the sum of the second preset threshold value and the adjustment value of second preset threshold value, the trigger time of image scanning may also be adjusted. In an embodiment, the adjustment value of second preset threshold value is 20% of the second preset threshold value, and the user may also manually turn off the similar-target triggering mechanism.

In regard to the auto mode, the preset threshold value is determined according to the proposed model for preset threshold value. The preset-threshold-value proposing model learns based on the contrast medium concentration, the shape of the patient, and other differential factors, and then proposes the threshold value. The threshold value is proposed automatically once the user selects a corresponding anatomical part, and the user needs not to set a corresponding threshold value. Similar to the case of the manual mode, when the CT number of the target part is within the range related to the first preset threshold value, the trigger time of image scanning may be adjusted. When the CT number of the similar target is within the range related to the second preset threshold value, namely the range in which the CT numbers are greater than or equal to the difference between the second threshold value and the adjustment value of second threshold value, and less than or equal to the sum of the second threshold value and the adjustment value of second threshold value, the trigger time of image scanning may also be adjusted. The user may also manually turn off the similar-target triggering mechanism.

In an embodiment of the control method for image scanning of the present disclosure, step S104 of generating the CT control parameter based on the CT number of the ROI and adjusting the trigger time of image scanning according to the CT control parameter may include step S301 and S302.

In step S301, the CT number of the first ROI or second ROI is obtained.

In step S302, the trigger time of image scanning for the monitoring layer is controlled according to the CT number.

Figure 6:
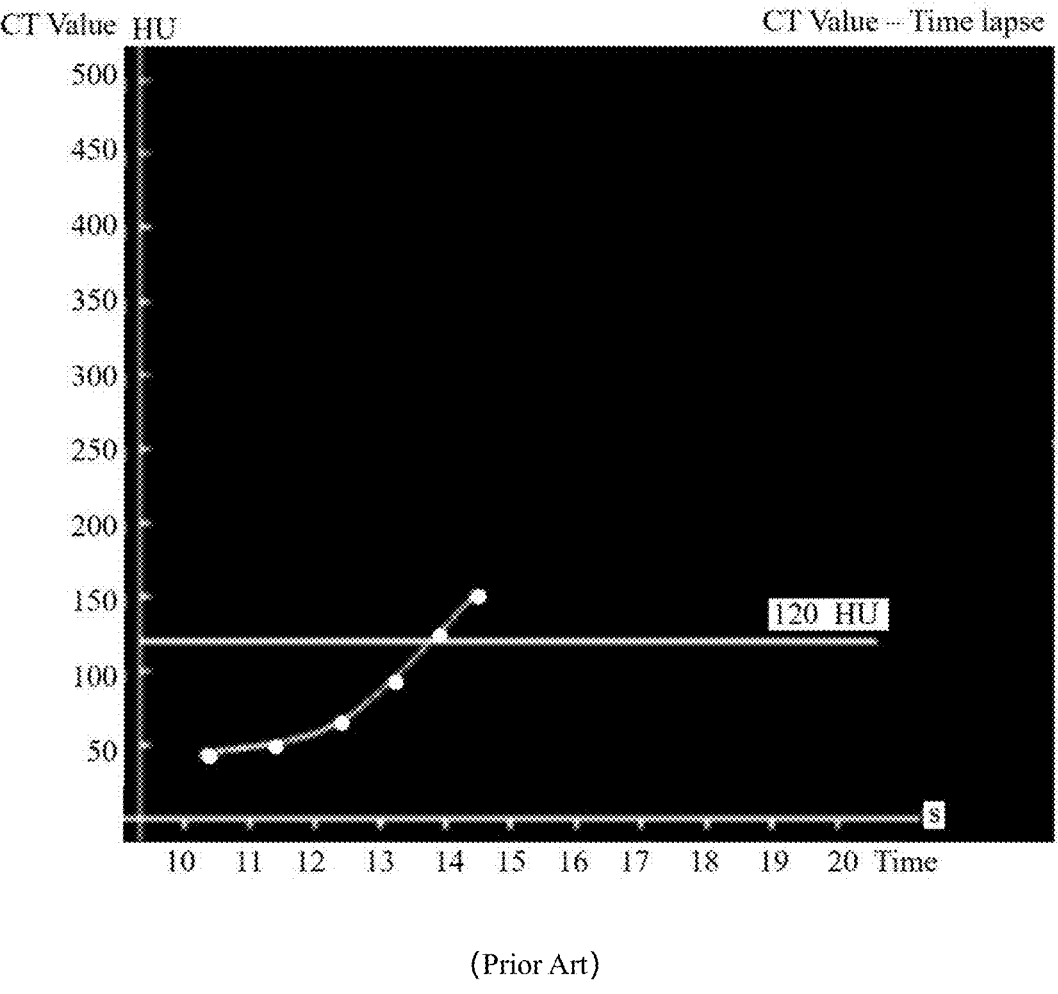
FIG. 6 is a schematic diagram showing exposure intervals in the related art.
Figure 7:
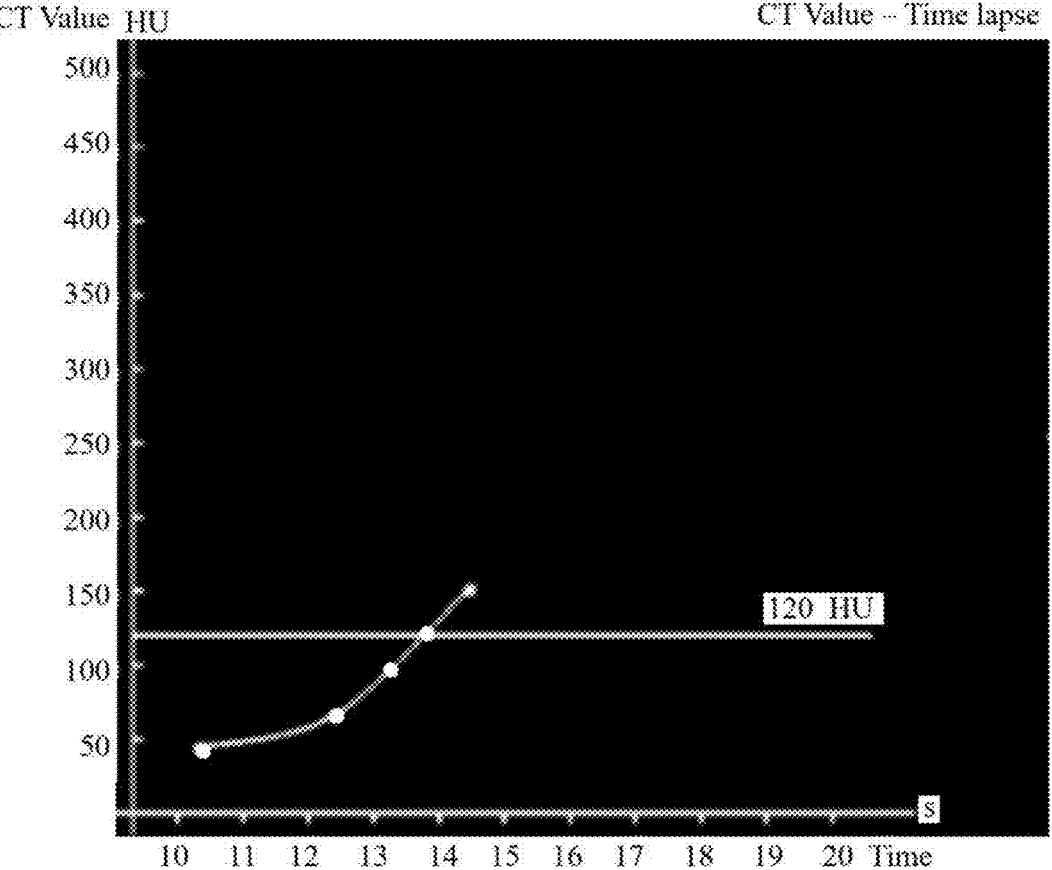
FIG. 7 is a schematic diagram showing exposure intervals according to an embodiment of the present disclosure.

It should be noted that in this embodiment of the present application, the adjusting the trigger time of image scanning may be achieved by controlling an exposure interval of CT. The adaptive exposure interval of the monitoring-layer scanning may reduce unnecessary scanning. As shown in FIG. 6, the exposure intervals in the related art are usually equal to each other, that is, exposure time points for the first scanning and the second scanning are fixed. In the figure, each white dot represents that an exposure occurs at a corresponding time point and when there is a corresponding CT number of the ROI. As shown in FIG. 7, the preset threshold value of the CT number of the ROI of the present disclosure is set to be 120HU, and when the CT number reaches to a value close to the preset threshold value, the time interval is shortened, that is, a sampling frequency of image is increased, or the exposure frequency is increased. In this way, the radiation dose is reduced, and the sampling frequency may be increased near the time to peak concentration, thereby improving the accuracy.

In the control method for image scanning of the embodiment of the present disclosure, the position of the ROI is updated in real time every time the monitoring layer is exposed, thus dynamically adjusting the position of the ROI of the target part (a vessel or an organ) and the position of the ROI of the similar part (a vessel or an organ), and ensuring accurate monitoring for the position of the ROI. In addition, the similar vessel on the same layer may also be extracted, thereby monitoring the plurality of ROIs to trigger scanning. What's more, the adaptive exposure occurs according to the CT number of the monitoring layer, thereby reducing the number of times of unnecessary exposure, reducing the radiation dose, increasing the sampling frequency near the time to peak concentration, and improving the accuracy.

Figure 8:
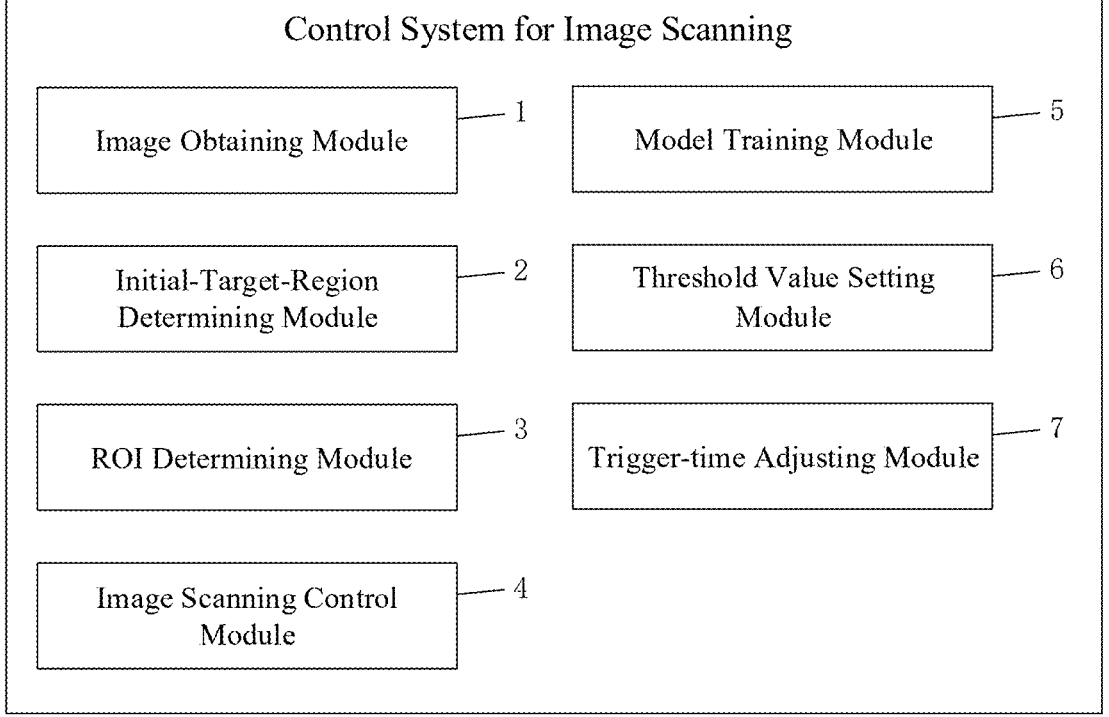
FIG. 8 is a schematic view showing modules of a control system for image scanning according to an embodiment of the present disclosure.

Corresponding to the control method for image scanning described above, an embodiment of the present disclosure also provides a control system for image scanning. As shown in FIG. 8, the control system for image scanning of the embodiment of the present disclosure includes an image obtaining module 1, an initial-target-region determining module 2, an ROI determining module 3, and an image scanning control module 4.

The image obtaining module 1 is configured to configure a monitoring-layer scanning, and obtain monitoring-layer images.

It should be noted that the monitoring-layer scanning is used for monitoring changes in CT numbers of a target part, that is, the changes in concentrations of the contrast medium in the target part. An image of a layer-plane, which may be, but not limited to, an axial image, or a sagittal image, may be obtained first through an axial scan. Specifically, the monitoring-layer scanning is to make continuous exposures for the same region/part to obtain monitoring-layer images at different time points, so as to determine a region of interest (ROI) based on the monitoring-layer images at different time points. The same part is scanned several times to obtain two-dimension images, and an exposure interval is 2 s. The exposure interval for the monitoring layer will be shortened to 0.5 s, when it is detected that the CT number of the ROI is approximate to a preset threshold value, namely within a range related to the preset threshold value, for example, within the range related to the preset threshold value in which the CT numbers are greater than or equal to a difference between the preset threshold value and 20% of the preset threshold value, and less than or equal to a sum of the preset threshold value and 20% of the preset threshold value. In an embodiment, the preset threshold value is 100, then the range related to the preset threshold value is from 80 to 120.

For example, the patient's target part may be first scanned to obtain a positioning image, for example, in the head and neck CTA scanning, the neck needs to be positioned. A position of the positioning image is selected based on the scanned positioning image, and the position of the monitoring layer is determined based on the position of the positioning image by, for example, dragging a scanning frame to change a position of the scanning frame. Then the contrast medium is injected, and continuous exposures are made to monitor and obtain the monitoring-layer image of the neck.

It should also be noted that the contrast medium is a chemical product injected into human tissues or organs to enhance the effect of image monitoring, or the contrast medium is taken orally by the patient and enters the patient's body. Because a density of the contrast medium is higher or lower than those of the surrounding tissues, the monitoring layer images may be obtained by means of some medical apparatus. These medical apparatuses mainly refer to medical image scanning devices, such as devices using computed tomography, any other scanning mode, or a combination thereof.

The initial-target-region determining module 2 is configured to determine an initial target region in each of the monitoring-layer images, and a target part is located in the initial target region.

The initial target region, namely an initial region in which the target part is located, is determined in the monitoring layer image. The initial region may be a region selected by the user roughly, and the roughly selected region is a closed region. For example, the user may draw or circle the target part in the monitoring-layer image through an input device, or a rough region may be automatically pre-selected based on the scanned project combining with historical data and human body data. For example, in the head and neck CTA scanning, a region of the carotid artery or a region of the vertebral artery in the neck may be pre-selected, which is also applicable to a coronary artery CTA, a cerebrovascular CTA, and a pulmonary artery CTA, which is not limited by the embodiments of the present disclosure. The determining the initial target region automatically or manually is provided by the embodiments of the present disclosure, so that even an inexperienced user may perform the operation, thereby improving user experience.

The ROI determining module 3 is configured to identify the target part in the initial target region, and determine a region corresponding to the identified target part to be the region of interest (ROI).

The target part is identified based on the initial target region determined by the user. Different tissue structures have different densities, shapes, and sizes, therefore pixels with similar CT numbers may be extracted based on the above characteristics, so that the edge of the target part may be identified, thereby obtaining an accurate region corresponding to the target part, and determining the region corresponding to the target part to be the ROI. In this way, even if the patient makes actions or slightly moves in the CTA scanning process without being noticed by the operator, real-time calculations may be performed to dynamically determine the ROI every time the monitoring layer is scanned, thereby ensuring the ROI is accurately monitored, and establishing a basis for accurately determining the time to peak concentration of the target part.

The image scanning control module 4 is configured to generate a CT control parameter based on the CT number of the ROI, and adjust a trigger time of image scanning according to the CT control parameter.

The trigger time of image scanning is the CT sampling and exposure time point. The CT sampling and exposure time point is adjusted according to the CT control parameter, so as to trigger the CT scanning according to the trigger time of image scanning.

In some embodiments of the present disclosure, the CT control parameter may be generated when the CT number of the ROI is within a range related to the preset threshold value. In some embodiments, the range related to the preset threshold value is a range in which the CT numbers are greater than or equal to a difference between the preset threshold value and an adjustment value of the preset threshold value, and are less than or equal to a sum of the preset threshold value and the adjustment value of the preset threshold value. In some embodiments, the adjustment value of the preset threshold value is 20% of the preset threshold value. For example, if the preset threshold value is 100, then the adjustment value of the preset threshold value is 20, and the range related to the preset threshold value is from 80 to 120.

It should be noted that the CT number is represented by a specific unit, generally a number called Hounsfield unit (HU), and represents the density of a certain local tissue or organ in the human body. The density of the contrast medium is generally higher or lower than the densities of the surrounding human tissues. In order to obtain the images with the optimal effect, the image scanning generally starts when the contrast medium concentration in the vessel in the target region is relatively high, that is, when the CT number of the target region (e.g., a vessel) is at a relatively high level.

That is to say, the embodiment of the present disclosure may accurately determine the corresponding ROI of the target part, and then determine the optimal scanning time point. That is, when the CT number of the ROI is within the range related to the preset threshold value, the trigger time of image scanning is adjusted, thereby accurately determining the ROI, obtaining the trigger time that enables the scanning effect to be the optimal, and obtaining the optimal image data.

As an optional implementation of the present disclosure, the initial target region includes a first initial target region, and correspondingly, the target part includes a first target part, the determined ROI includes a first ROI, the preset threshold value includes a first preset threshold value, and the range related to the preset threshold value includes a range related to the first preset threshold value.

The ROI determining module 3 is further configured to determine a center point of the first initial target region, extract similar pixels centered around the center point to identify an edge of the first target part, and determine a region within the edge of the first target part to be the first ROI.

A geometric center of the first initial target region determined by the user is extracted and is determined to be the center point of the first initial target region. The initial target region is generally in a shape of an ellipse or a circle, or has an irregular shape. For example, if the first initial target region determined by the user is in the shape of a circle, then the center point of the first initial target region is the center of the circle.

The operation of pixel erosion and expansion is performed by means of spreading from the determined center point of the first initial target region to extract similar pixels nearby, so that a boundary or edge of the first target part is identified.

The outcome of processing is updated and displayed as the first ROI, so that the time to peak concentration of the contrast medium of the first target part is accurately monitored.

The image scanning control module 4 is further configured to generate a CT control parameter if the CT number of the first ROI is within the range related to the first preset threshold value, and adjust the trigger time of image scanning according to the CT control parameter.

In an embodiment of the present disclosure, if the CT number of the first ROI within the ROI is within the range related to the first preset threshold value, the CT control parameter is generated to adjust the trigger time of image scanning.

According to the embodiments of the present disclosure, after the rough region is determined, the region corresponding to the first target part may be accurately identified and is determined to be the first ROI, then it may be determined whether the CT number of the first ROI is within the range related to the first preset threshold value, so as to determine whether the trigger time of image scanning needs to be adjusted or not.

In another optional embodiment of the present disclosure, the initial target region further includes a second initial target region, and correspondingly, the target part further includes a second target part, the determined ROI further includes a second ROI, the preset threshold value further includes a second preset threshold value, and the range related to the preset threshold value further includes the range related to the second preset threshold value. In an embodiment, a time to peak concentration of the contrast medium of the second target part is substantially identical to the time to peak concentration of the contrast medium of the first target part.

It should be noted that the second initial target region is not limited to one part or one region, and may include a plurality of parts or regions, that is, as long as a part or region (e.g., a vessel or an organ) and the first target part have the substantially identical time to peak concentration of the contrast medium, the part or region may be used as the second ROI. Therefore, the number of the second initial target regions is not limited in the embodiments of the present disclosure.

The ROI determining module 3 is further configured to identify the second target part in the second initial target region in the monitoring-layer image based on the first target part, and determine the second ROI corresponding to the second target part.

Identify and segment the anatomical locations on the same monitoring layer, and all similar parts, namely the second target parts, like vessels or organs, are extracted. The similar vessels refer to the vessels, through which the blood flows by taking the substantially identical flow time period during a blood circulation, thus the similar vessels may be used to determine the time to peak concentration of the contrast medium.

In an optional embodiment, the ROI determining module 3 is further configured to identify the second target part in the second initial target region in the monitoring-layer image based on the first target part and a preset similar-target identification model, and determine a region within the edge of the second target part to be the second ROI.

For example, the left and right common carotid arteries and the left and right vertebral arteries in the neck have a substantially identical time to peak concentration, so no matter which one of the vessels is used as the first target part (a target vessel), the other three vessels may be used as the second target parts (similar vessels).

It should also be noted that the second target part in the second initial target region in the monitoring-layer image is identified based on the first target part and the preset similar-target identification model. After the second target part is determined, the second initial target region is updated in real time to obtain the second ROI. An updating process of the second initial target region is similar to the updating process of the first initial target region in which the similar pixels from the center point to the edge are extracted, and will not be repeated hereinafter.

In some embodiments of the present disclosure, the image scanning control system further includes a model training module 5.

The model training module 5 is configured to obtain historical scanned images of different body parts, mark target parts having a substantially identical time to peak concentration or a substantially identical flow rate in the historical scanned images to obtain a data set, and input the data set into an identification model for target, and train the identification model for target to obtain the preset similar-target identification model.

It should be noted that the data set mainly includes enhanced scanned images obtained after the contrast medium is injected. These enhanced scanned images obtained at different time points are analyzed to identify vessels having the substantially identical time to peak concentration in different body parts, and these vessels are marked.

The image scanning control module 4 is further configured to generate the CT control parameter if the CT number of the second ROI is within the range related to the second preset threshold value, and adjust the trigger time of image scanning according to the CT control parameter.

In an embodiment of the present disclosure, the CT control parameter may also be generated when the CT number of the second ROI within the ROI is within the range related to the second preset threshold value, so as to adjust the trigger time of image scanning.

In some embodiments of the present disclosure, the similar parts in the same layer-plane, namely the second target parts, may be extracted to identify the plurality of second ROIs and trigger the scanning, thereby solving the problem that the ROIs in small vessels in the body part cannot be precisely positioned because the contrast medium is not full and the CT number is inaccurate, which is caused by pathologic factors such as plaques in target vessels, calcification of the target vessels, etc. Thus, the time to peak concentration of the contrast medium is accurately captured by using the similar parts, thereby guaranteeing of obtaining the optimal image data.

In some embodiments of the present disclosure, the control system for image scanning further includes a threshold value setting module 6.

The threshold value setting module 6 is configured to determine the preset threshold value corresponding to the target part based on a proposed model for preset threshold value.

In some embodiments of the present disclosure, the threshold value setting module 6 is configured to obtain the preset threshold value of the CT number of the ROI based on medical experience. The preset threshold value can be set based on known medical experience. The preset threshold value may be set based on known medical experience, and a specific value thereof depends on different to-be-scanned target parts of different patients and is not specifically limited in the embodiments of the present disclosure.

It should be noted that the threshold value setting modes of the embodiments of the present disclosure include a manual mode and an auto mode. The range related to the preset threshold value is a range in which the CT numbers are greater than or equal to the difference between the preset threshold value and the adjustment value of the preset threshold value, and are less than or equal to the sum of the preset threshold value and the adjustment value of the preset threshold value. The manual mode means that the user needs to set the preset threshold value manually. When the CT number of the target part is within the range related to the first preset threshold value, the trigger time of image scanning may be adjusted. When the CT number of the similar target is within the range related to the second preset threshold value, namely the range in which the CT numbers are greater than or equal to the difference between the second preset threshold value and the adjustment value of second preset threshold value, and are less than or equal to the sum of the second preset threshold value and the adjustment value of second preset threshold value, the trigger time of image scanning may also be adjusted. In an embodiment, the adjustment value of second preset threshold value is 20% of the second preset threshold value, and the user may also manually turn off the similar-target triggering mechanism.

In regard to the auto mode, the preset threshold value is determined according to the proposed model for preset threshold value. The preset-threshold-value proposing model learns based on the contrast medium concentration, the shape of the patient, and other differential factors, and then proposes the threshold value. The threshold value is proposed automatically once the user selects a corresponding anatomical part, and the user needs not to set a corresponding threshold value. Similar to the case of the manual mode, when the CT number of the target part is within the range related to the first preset threshold value, the trigger time of image scanning may be adjusted. When the CT number of the similar target is within the range related to the second preset threshold value, namely the range in which the CT numbers are greater than or equal to the difference between the second threshold value and the adjustment value of second threshold value, and less than or equal to the sum of the second threshold value and the adjustment value of second threshold value, the trigger time of image scanning may also be adjusted. The user may also manually turn off the similar-target triggering mechanism.

In an embodiment of the present disclosure, the control system of image scanning further includes a trigger-time adjusting module 7.

The trigger-time adjusting module 7 is configured to obtain the CT number of the first ROI or second ROI, and adjust the trigger time of image scanning for the monitoring layer according to the CT number.

It should be noted that in some embodiments of the present application, the adjusting the trigger time of image scanning may be achieved by controlling an exposure interval of CT. The adaptive exposure interval of the monitoring-layer scanning may reduce unnecessary scanning. For example, the preset threshold value of the CT number of the ROI is set to be 120HU, and when the CT number reaches to a value close to the preset threshold value, the time interval is shortened, that is, the exposure frequency is increased. In this way, the radiation dose is reduced, and the sampling frequency may be increased near the time to peak concentration, thereby improving the accuracy.

In the control method for image scanning of the embodiment of the present disclosure, the position of the ROI is updated in real time every time the monitoring layer is exposed, thus dynamically adjusting the position of the ROI of the target part (a vessel or an organ) and the position of the ROI of the similar part (a vessel or an organ), and ensuring accurate monitoring for the position of the ROI. In addition, the similar vessel on the same layer may also be extracted, thereby monitoring the plurality of ROIs to trigger scanning. What's more, the adaptive exposure occurs according to the CT number of the monitoring layer, thereby reducing the number of times of unnecessary exposure, reducing the radiation dose, increasing the sampling frequency near the time to peak concentration, and improving the accuracy.

It should be noted that the control system for image scanning in an embodiment of the present disclosure may be a separate chip, a chip module, an electronic apparatus, or a chip or a chip module integrated in an electronic apparatus. In regard to various modules/units included in each device and product described in the above embodiments, they may be software modules/units or hardware modules/units, or some of them are software modules/units and some of them are hardware modules/units. For example, for various devices and products applied to or integrated in a chip, each module/unit included therein can be implemented in the form of hardware such as circuits, or at least some of the modules/units may be implemented in the form of a software program, where, the software program is run by the processor integrated inside the chip, the remaining (if any) modules/units may be implemented by hardware such as circuits. In regard to various devices and products applied to or integrated in the chip module, each module/unit included therein may all be implemented in the form of hardware such as circuits, and different modules/units may be located in the same component of the chip module, such as a chip, and a circuit module, etc., or located in different components, and alternatively, at least some modules/units may be implemented in the form of a software program, and the software program is run by the processor integrated in the chip module, and the remaining (if any) modules/units may be implemented by hardware such as circuits. In regard to various devices or products applied to or integrated in a terminal, various modules/units included therein may all be implemented by hardware such as circuits, and different modules/units may be located in the same component (for example, chip, circuit module, etc.) or in different components within the terminal, or at least some of the modules/units may be implemented in the form of a software program, and the software program is run by the processor integrated in the terminal, and the remaining (if any) modules/units may be implemented by hardware such as circuits.

Figure 9:
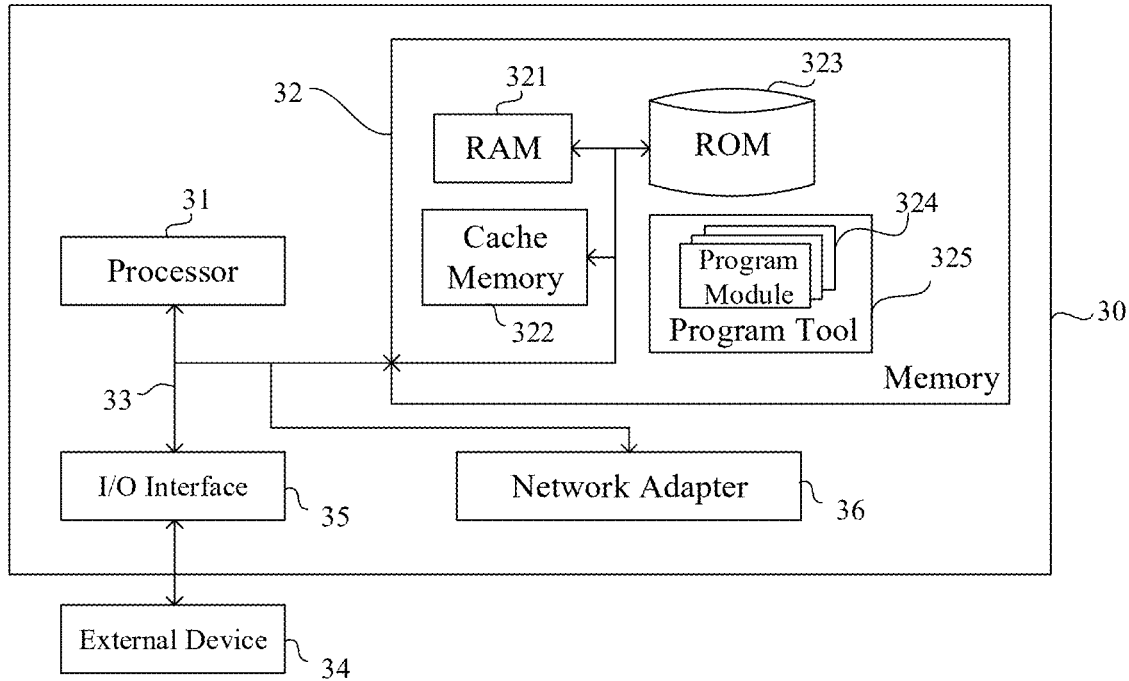
FIG. 9 is a schematic view showing a structure of an electronic apparatus implementing the control method for image scanning according to an embodiment of the present disclosure.

FIG. 9 is a schematic view showing a structure of an electronic apparatus according to an embodiment of the present disclosure. The electronic apparatus includes a memory, a processor, and a computer program stored in the memory and executable by the processor. The processor, when executing the program, implements the steps of the control method for image scanning of the above embodiment. The electronic apparatus 30 shown in FIG. 9 is merely an example and should not limit the functionality and scope of application of the embodiments of the present disclosure.

As shown in FIG. 9, the electronic apparatus 30 may be in the form of a general computing device, for example, may be a server device. The components of the electronic apparatus 30 may include, but are not limited to, the at least one processor 31, the at least one memory 2, and a bus 3 connecting different system components including the memory 32 and the processor 31.

The bus 33 includes a data bus, an address bus, and a control bus.

The memory 32 may include a volatile memory, such as a random-access memory (RAM) 321 and/or a cache memory 322, and may further include a read-only memory (ROM) 323.

The memory 32 may also include a program/utility tool 325 having a set of (at least one) program module(s) 324. The program module 324 includes, but not limited to, an operating system, one or more application programs, other program modules, and program data. Each of the examples or some combination of these examples may include an implementation of a network environment.

When running the computer program stored in the memory 32, the processor 31 performs various functional applications and a data processing, such as the method of nidus segmentation of an embodiment described above.

The electronic apparatus 30 may also communicate with one or more external devices 34 (e.g., a keyboard, a pointing device, etc.). Such communication may be realized through an input/output (I/O) interface 35. Also, the electronic apparatus 3 may also communicate with one or more networks, such as a local area network (LAN), a wide area network (WAN), and/or a public network (e.g., the Internet), through a network adapter 36. As shown in FIG. 9, the network adapter 36 communicates with other modules of the electronic apparatus 30 via the bus 33. It should be understood that, although not shown in the figure, other hardware and/or software modules including, but not limited to, a microcode, a device driver, a redundant processor, an external disk drive array, a system of redundant arrays of independent disks (RAID), a tape driver, and a data backup storage system, etc., may be used in conjunction with the electronic apparatus 30.

It should be noted that although several units/modules or sub-units/modules of the electronic apparatus are mentioned in the above detailed description, this division is merely exemplary and not mandatory. Indeed, according to the embodiments of the present disclosure, the features and functions of two or more units/modules described above may be specified in one unit/module. Conversely, the features and functions of one unit/module described above may be further divided and specified by a plurality of units/modules.

An embodiment of the present disclosure provides a non-transitory computer readable storage medium having a computer program stored thereon, which, when executed by a processor, causes the processor to perform the control method for image scanning of the embodiments above.

More specifically, the readable storage medium may include, but is not limited to, a portable disk, a hard disk, a random-access memory, a read-only memory, an erasable programmable read-only memory, an optical memory device, a magnetic memory device, or any proper combination thereof.

In a possible embodiment, the present disclosure may also be implemented in the form of a program product including a program code. The program causes the electronic apparatus to perform the control method for image scanning of the embodiments of the present disclosure when the program product is run on the electronic apparatus.

The program code for implementing the present disclosure may be written with one programming language or any combination of more programming languages, and the program code may be executed entirely on the electronic apparatus, executed partly on the electronic apparatus, executed as a separate software package, executed partly on the electronic apparatus and partly on a remote device, or executed entirely on the remote device.

Although specific embodiments of the present disclosure have been described above, it should be understood by those skilled in the art, that these embodiments are merely illustrative, and that the scope of the present disclosure is defined by the appended claims. Various changes or modifications may be made to these implementations by those skilled in the art without departing from the principles and essences of the disclosure, but these changes and modifications are within the scope of the disclosure.

What is claimed is:

1. A control method for image scanning, comprising:
configuring a monitoring-layer scanning, and obtaining monitoring-layer images;
determining an initial target region in each of the monitoring-layer images, a target part being located in the initial target region;
identifying the target part in the initial target region, and determining a region corresponding to the identified target part to be a region of interest (ROI); and
generating a computed tomography (CT) control parameter based on a CT number of the ROI, and adjusting a trigger time of image scanning according to the CT control parameter;
wherein the initial target region comprises a first initial target region and a second initial target region, the target part comprises a first target part and a second target part, and the ROI comprises a first ROI and a second ROI; and
identifying the target part in the initial target region and determining the region corresponding to the identified target part to be the ROI comprises:
determining a center point of the first initial target region;
extracting similar pixels centered around the center point to identify an edge of the first target part;
determining a region within the edge of the first target part to be the first ROI;
obtaining historical scanned images of different body parts;
marking target parts having an identical time to peak concentration or having an identical flow rate in the historical scanned images to obtain a data set;
inputting the data set into an identification model for target, and training the identification model for target to obtain a preset target identification model;
identifying the second target part in the second initial target region in each of the monitoring-layer images based on the first target part and the preset target identification model; and
determining a region within an edge of the second target part to be the second ROI.

2. The control method for image scanning according to claim 1, wherein, before the generating the CT control parameter based on the CT number of the ROI and adjusting the trigger time of image scanning according to the CT control parameter, the control method for image scanning further comprises: setting a preset threshold value of the CT number of the ROI.

3. The control method for image scanning according to claim 2, wherein the generating the CT control parameter based on the CT number of the ROI and adjusting the trigger time of image scanning according to the CT control parameter, comprises:

generating the CT control parameter when the CT number of the ROI is within a range related to the preset threshold value, and adjusting the trigger time of image scanning according to the CT control parameter.

4. The control method for image scanning according to claim 3, wherein the range related to the preset threshold value is a range, in which CT numbers are greater than or equal to a difference between the preset threshold value and an adjustment value of the preset threshold value, and are less than or equal to a sum of the preset threshold value and the adjustment value of the preset threshold value.

5. The control method for image scanning according to claim 4, wherein the adjustment value of the preset threshold value is 5%, 10%, 15%, 20%, or 25% of the preset threshold value.

6. The control method for image scanning according to claim 3, wherein:

the preset threshold value comprises a first preset threshold value, and the range related to the preset threshold value comprises a range related to the first preset threshold value.

7. The control method for image scanning according to claim 6, wherein the generating the computed tomography control parameter based on the CT number of the ROI and adjusting the trigger time of image scanning according to the CT control parameter, comprises:

generating the CT control parameter if a CT number of the first ROI is within the range related to the first preset threshold value, and adjusting the trigger time of image scanning according to the CT control parameter.

8. The control method for image scanning according to claim 6, wherein:

the preset threshold value further comprises a second preset threshold value, and the range related to the preset threshold value further comprises a range related to the second preset threshold value.

9. The control method for image scanning according to claim 8, wherein the first preset threshold value is the same as the second preset threshold value.

10. The control method for image scanning according to claim 9, wherein the range related to the first preset threshold value is the same as the range related to the second preset threshold value, and a time to peak concentration of contrast medium of the second target part is identical to a time to peak concentration of contrast medium of the first target part.

11. The control method for image scanning according to claim 8, wherein the generating the CT control parameter based on the CT number of the ROI and adjusting the trigger time of image scanning according to the CT control parameter, comprises:

generating the CT control parameter if a CT number of the second ROI is within the range related to the second preset threshold value, and adjusting the trigger time of image scanning according to the CT control parameter.

12. The control method for image scanning according to claim 2, wherein the setting the preset threshold value of the CT number of the ROI comprises:

determining the preset threshold value of the CT number of the ROI based on a preset-threshold-value proposing model; or obtaining the preset threshold value of the CT number of the ROI based on medical experience.

13. The control method for image scanning according to claim 7, wherein:

the range related to the first preset threshold value is a range, in which CT numbers are greater than or equal to a difference between the first preset threshold value and an adjustment value of the first preset threshold value, and are less than or equal to a sum of the first preset threshold value and the adjustment value of the first preset threshold value; and the adjustment value of the first preset threshold value is 20% of the first preset threshold value.

14. The control method for image scanning according to claim 11, wherein:

the range related to the second preset threshold value is a range, in which CT numbers are greater than or equal to a difference between the second preset threshold value and an adjustment value of the second preset threshold value, and are less than or equal to a sum of the second preset threshold value and the adjustment value of the second preset threshold value; and the adjustment value of the second preset threshold value is 20% of the second preset threshold value.

15. The control method for image scanning according to claim 8, wherein:

the initial target region comprises a plurality of second initial target regions, the target part comprises a plurality of second target parts, the ROI comprises a plurality of second ROIs, the preset threshold value comprises a plurality of second preset threshold values, and the range related to the preset threshold value comprises a plurality of ranges related to the plurality of second preset threshold values, respectively; and after the determining the region within the edge of the first target part to be the first ROI, the control method for image scanning further comprises:

identifying the plurality of second target parts in the plurality of second initial target regions in each of the monitoring-layer images based on the first target part, and determining the plurality of second ROIs corresponding to the plurality of second target parts, respectively.

16. The image scanning triggering method according to claim 8, wherein the generating the CT control parameter based on the CT number of the ROI and adjusting the trigger time of image scanning according to the CT control parameter, comprises:

obtaining the CT number of the first ROI or the CT number of the second ROI; and increasing a sampling frequency of image when the CT number of the first ROI is within the range related to the first preset threshold value, or when the CT number of the second ROI is within the range related to the second preset threshold value.

17. An electronic apparatus, comprising a memory, a processor, and a computer program stored in the memory and executable by the processor, wherein the processor, when executing the computer program, executes steps of the control method of claim 1.

18. A non-transitory computer-readable storage medium, having a computer program stored thereon, wherein the computer program, when executed by a processor, causes the processor to execute steps of:

configuring a monitoring-layer scanning, and obtaining monitoring-layer images;

determining an initial target region in each of the moni-
toring-layer images, a target part being located in the
initial target region;
identifying the target part in the initial target region and
determining a region corresponding to the identified
target part to be a region of interest (ROI); and
generating a computed tomography (CT) control param-
eter based on a CT number of the ROI, and adjusting a
trigger time of image scanning according to the CT
control parameter;
wherein the initial target region comprises a first initial
target region and a second initial target region, the
target part comprises a first target part and a second
target part, and the ROI comprises a first ROI and a
second ROI; and
identifying the target part in the initial target region and
determining the region corresponding to the identified
target part to be the ROI comprises:
determining a center point of the first initial target
region;
extracting similar pixels centered around the center
point to identify an edge of the first target part;
determining a region within the edge of the first target
part to be the first ROI;
obtaining historical scanned images of different body
parts;
marking target parts having an identical time to peak
concentration or having an identical flow rate in the
historical scanned images to obtain a data set;
inputting the data set into an identification model for
target, and training the identification model for target
to obtain a preset target identification model;
identifying the second target part in the second initial
target region in each of the monitoring-layer images
based on the first target part and the preset target
identification model; and determining a region within an edge of the second
target part to be the second ROI.
19. A control method for image scanning, comprising:
configuring a monitoring-layer scanning, and obtaining
monitoring-layer images;
determining an initial target region in each of the moni-
toring-layer images, a target part being located in the
initial target region;
identifying the target part in the initial target region, and
determining a region corresponding to the identified
target part to be a region of interest (ROI) and the ROI
comprising a first ROI;
setting a preset threshold value of a computed tomogra-
phy (CT) number of the ROI, and the preset threshold
value comprising a first preset threshold value; and
generating a CT control parameter based on the CT
number of the ROI, and adjusting a trigger time of
image scanning according to the CT control parameter;
wherein generating the CT control parameter based on the
CT number of the ROI comprises:
generating the CT control parameter when a CT number
of the first ROI is within a range related to the first
preset threshold value;
wherein the range related to the first preset threshold
value is a range, in which CT numbers are greater than
or equal to a difference between the first preset thresh-
old value and an adjustment value of the first preset
threshold value, and are less than or equal to a sum of
the first preset threshold value and the adjustment value
of the first preset threshold value; and
the adjustment value of the first preset threshold value is
20% of the first preset threshold value.

* * * * *